| [11] | 4,362,550 |
| --- | --- | --- |
| | [45] | Dec. 7, 1982 |

[54] HERBICIDAL TRIAZINONES

[75] Inventor: John L. Miesel, Indianapolis, Ind.

[73] Assignee: Eli Lilly and Company, Indianapolis, Ind.

[21] Appl. No.: 333,134

[22] Filed: Dec. 21, 1981

[51] Int. Cl.³ .................... C07D 253/06; A01N 43/64
[52] U.S. Cl. ......................................... 71/93; 544/182
[58] Field of Search ............................. 544/182; 71/93

[56] References Cited

U.S. PATENT DOCUMENTS 4,033,752 7/1977 Hashimoto et al. .................... 71/93
4,081,267 3/1978 Hashimoto et al. .................... 71/93

OTHER PUBLICATIONS

Adembri et al., *Tetrahedron Letters*, No. 45, pp. 4439–4442, (1978).
Charles et al., *J. Chem. Soc., Perkin Tran. 1*, (1980), pp. 1139–1146.
Chaloupka et al., *Chimia*, vol. 32, pp. 332–333, (1978).
Link, *Helv. Chim. Acta*, vol. 61, pp. 2419–2427, (1978).
Camprarini et al., *Chem. Abstracts*, vol. 90, entry 168552p, (1979).
Nalepa, *Monatsh. Chem.*, vol. 98, pp. 412–416, (1967).
Nalepa, *J. Prakt. Chem.*, vol. 314, pp. 851–856, (1972).
Nelepa, *Chem. Abstracts*, vol. 95, entry 80898y, (1981).
Nishiwaki, *Chem. Abstracts*, vol. 74, entry 53737e, (1971).
Nyitra, *Chem. Abstracts*, vol. 89, entry 215367y, (1981).
Becker et al., *J. Prakt. Chem.*, vol. 312, pp. 669–682, (1970).
Nalepa et al., *Coll. Czech. Chem. Commun.*, vol. 42, pp. 2182–2185, (1977).
Nishiwaki et al., *J. Chem. Soc., C,* (1971), pp. 2648–2652.
Camparini et al., "Synthesis and Structure of Dihydro—1,2,4—triazin—6(1H)—ones", *J. Het. Chem.*, 15, 1271, (1978).
Domany et al., "The Reaction . . . as—Triazinones", *Tet. Let.*, No. 16, 1393, (1977).
Lobanov et al., "Ring—Chain . . . Hydrazines", *Translated from Zhurnal Organicheskoi Khimii*, vol. 16, No. 11, 2297, (1980).
Kirino et al., "3—(2'-Pyridyl) . . . Herbicides", *Agric. Biol. Chem.*, 41(6), 1093, (1977).
Camparini et al., "Synthesis and Structure of 1,2,4—triazin—6—ones", *C.A.*, 85:94321k, (1976).
Kjaer, A., "Reactions . . . Esters", *Acta. Chem. Scand.*, 7, 1024, (1953).
Camparini et al., "Sintesi . . . 1,2,4—triazin—6—oni", *Chim. Ind.*, 58(3), 221, (1976).

*Primary Examiner*—John M. Ford
*Attorney, Agent, or Firm*—Kathleen R. S. Page; Arthur R. Whale

[57] ABSTRACT

1,2,4-Triazin-6(1H)-ones, useful as herbicides.

17 Claims, No Drawings

HERBICIDAL TRIAZINONES

SUMMARY OF THE INVENTION

The present invention relates to a compound of the formula

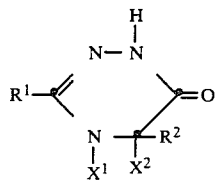

wherein:

$R^1$ represents $C_1$–$C_6$ alkyl, $C_3$–$C_6$ cycloalkyl, phenyl or phenyl monosubstituted with $C_1$–$C_3$ alkyl, $C_1$–$C_3$ alkoxy, halogen, $C_1$–$C_3$ haloalkyl or $C_1$–$C_3$ haloalkoxy;

$R^2$ represents hydrogen, $C_1$–$C_6$ alkyl or $C_3$–$C_6$ cycloalkyl; and $X^1$ and $X^2$ represent hydrogen atoms or combine to form a carbon-carbon bond;

with the provisos that when $R^2$ is methyl, $R^1$ is other than phenyl; and when $X^1$ and $X^2$ combine to form a carbon-carbon bond and $R^2$ is ethyl, $R^1$ is other than phenyl, 4-chlorophenyl and 4-methoxyphenyl.

The present invention also provides a herbicidal method for the use of the present novel compounds, as well as compositions containing such compounds.

DETAILED DESCRIPTION OF THE INVENTION

The compounds of the present invention are preferably prepared by a process well known to those skilled in the art. This method of preparation involves reacting a glycine alkyl ester derivative with a substituted acid halide derivative to give the corresponding amide ester. The amide ester is reacted with phosphorus pentasulfide to give the substituted thioamide ester analog, which is reacted with an alkyl halide and sodium alkoxide to give the corresponding thioimino ether. This compound is finally reacted with hydrazine to give a 4,5-dihydro-1,2,4-triazin-6-one derivative of the present invention. The scheme for this reaction is as follows:

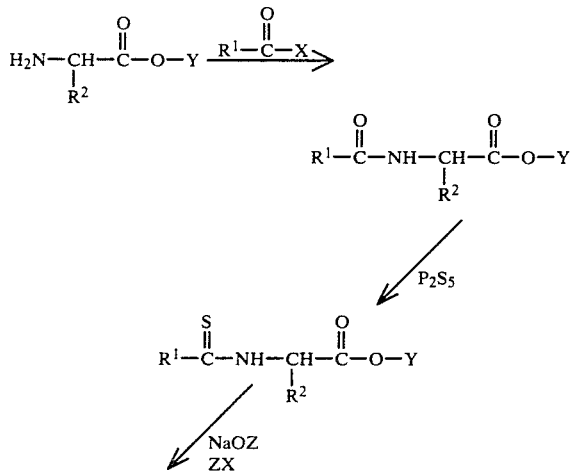

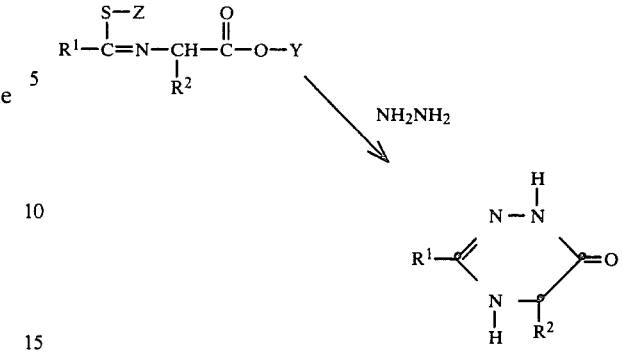

wherein X represents halogen, Y represents $C_1$–$C_4$ alkyl and Z represents $C_1$–$C_4$ alkyl.

The first step of this process involves acylating an α-amino acid derivative with an appropriately substituted acylating agent, for example an acid halide or anhydride analog. This procedure is well known to those skilled in the art.

The second step of the above described reaction process involves reacting an amide ester with phosphorous pentasulfide to give the corresponding thioamide ester. This reaction is generally performed in a hydrocarbon solvent such as benzene, toluene, the xylenes, hexane, octane and the like. Benzene, toluene and the xylenes are preferred. The temperature range suitable for addition of the reactants can be from 0° C. to 30° C. with 10° C. to 25° C. being preferred. Usually following addition of the reactants the temperature of the reaction mixture is increased to about 40° C. to 140° C., more preferably to the reflux temperature of the reaction mixture. The reaction is then worked up according to standard procedures. Typically, the solid is collected or the filtrate is concentrated in vacuo. The product then can be further purified by either crystallization or column chromatography.

The third step of the preferred reaction procedure used to prepare compounds of the present invention involves reacting the thioamide ester with sodium alkoxide and an alkyl halide to give the corresponding thioimino ether. Preferred reactants include sodium methoxide and methyl iodide. Suitable solvents for this procedure include the alcohols, for example methanol and ethanol. The reactants are usually added to the mixture at a temperature in the range of from about −25° C. to 10° C., preferably about 0° C. to 5° C. The mixture is then usually stirred from about 1 to about 24 hours, and then allowed to warm to about 25° C. Typically the reaction mixture is worked up by pouring the mixture into an ice water-organic solvent mixture. The organic phase, typically ether, is then collected, dried and concentrated. The product should then be used immediately in the next step of the reaction procedure to prevent its decomposition.

The final step of the reaction process involves reacting the thioimino ether with hydrazine in a suitable solvent such as the alcohols, preferably methanol or ethanol. The temperature range suitable for addition of the hydrazine can be from about −20° C. to about 30° C., preferably at about 0° C. The reaction mixture is typically allowed to stir at this temperature for a time period of from about 1 to about 4 hours. The mixture is then gradually warmed to a temperature of about 20° C. to 150° C., or the reflux temperature of the mixture, as required, until formation of the product has taken place. The reaction is then generally worked up by removing the solvent in vacuo, and purifying by standard procedures if desired.

Certain of the compounds of the present invention may be prepared by reacting a hippuric acid ester derivative with triphenyl phosphine and carbon tetrachloride in a suitable solvent to generate the chloro imino derivative, which is then reacted with hydrazine to give the corresponding 1,2,4-triazin-6-one. Suitable solvents for this reaction include most aprotic solvents with tetrahydrofuran being preferred. The mixture is usually heated to a temperature of about 30° to 100° C., or the reflux temperature of the reaction mixture. Following formation of the chloro intermediate, hydrazine is added. The reaction mixture is then stirred at a temperature in the range of 30° C. to 150° C., more preferably at the reflux temperature of the reaction mixture. The reaction is generally complete after about 1 to 24 hours. The product is then isolated by standard procedures. The mixture may be poured into water and extracted with a typical organic solvent. The product is extracted with acid, and the aqueous phase is neutralized with base. The product is then usually extracted with an organic solvent. The organic phase is then concentrated and the product purified according to well known procedures.

The compounds of the present invention wherein the triazinone ring is unsaturated may be prepared by oxidation procedures well known in the art as follows:

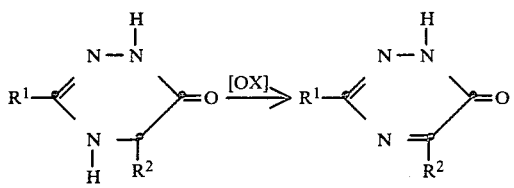

This reaction is preferably performed in a suitable solvent using any one of a broad class of known oxidizing agents, preferably DDQ (2,3-dichloro-5,6-cyano-1,4-benzoquinone). Suitable solvents for this reaction include most aprotic solvents such as ethyl acetate. Typically one equivalent of the oxidizing agent is added to the reaction mixture at a temperature of from about 0° C. to 100° C., more preferably 15° C. to 30° C. The mixture is generally stirred at this temperature until the reaction is complete, or the mixture may be heated to reflux, for example, to aid formation of the product. The reaction is then worked up according to standard procedures. Typically, after cooling the reaction mixture, the solid is collected or the solvent is removed in vacuo. The product may then be further purified by recrystallization or column chromatography.

A typical preparation of the starting materials used to prepare compounds of the present invention by the preferred process is represented by the following.

N-Benzoyl-L-valine, methyl ester

To 4.0 g. L-valine methyl ester hydrochloride dissolved in 25 ml water was added 3.35 g. benzoyl chloride while keeping the pH of the solution at approximately 8-9 with 1 N NaOH. The addition of the reactants took approximately 2 hours. Following addition of the reactants the reaction mixture was stirred at about 25° C. for 4 hours and then cooled to about 0° C. for 16 hours. The precipitated solid was collected and the filtrate was extracted twice with ether. The above collected solid was dissolved in this ether solution, which was then washed with a saturated sodium bicarbonate solution. The organic phase was dried and concentrated to give a white solid.

N-Thiobenzoyl-L-valine, methyl ester

To 3.0 g. N-benzoyl-L-valine, methyl ester dissolved in 50 ml benzene was added 0.56 g. phosphorus pentasulfide in one portion at 20° C. The mixture was refluxed for about 4 hours, cooled to about 20° C. and filtered. The resulting oil which was collected was washed with methylene chloride and filtered. The combined filtrates were concentrated under vacuum to yield a yellow oil. Column chromatography with silica gel and a hexane-ethyl acetate solvent system gave 1.89 g. (59%) of a yellow oil.

N-[2-(3-methyl)butyric acid methyl ester]-phenyl-(methylthio)imino ether

To 0.41 g. sodium methoxide dissolved in 20 ml methanol was added 1.8 g. N-thiobenzoyl-L-valine, methyl ester in 5 ml MeOH over a 2 minute period at about 0° C. Following addition the reaction mixture was allowed to stir for about four additional minutes, and 3.0 g. methyl iodide was added. The mixture was stirred for 5 hours and then allowed to warm to about 25° C. The mixture was poured into 25 ml of ice water and 75 ml ether. The organic phase was collected, washed with ice water, and dried over anhydrous magnesium sulfate. The solvent was removed in vacuo resulting in 1.72 g. yellow oil. The product was used immediately in the next step.

EXAMPLE 1

3-Phenyl-5-(1-methylethyl)-4,5-dihydro-1,2,4-triazin-6(1H)-one

To 1.72 g N-[2-(3-methyl)butyric acid methyl ester]-phenyl(methylthio)imino ether in 10 ml methanol at 5° C. was added 0.7 g. hydrazine hydrate dissolved in 1 ml methanol dropwise over a 1 minute period. The mixture was allowed to stir at about 5° C. for 2 hours. The ice bath was removed, the reaction mixture was stirred at about 25° C. for 20 hours, and then refluxed for about 2 hours. The volatiles were removed in vacuo. The resulting oil was dissolved in methylene chloride and washed with water. The organic phase was dried over anhydrous sodium sulfate and the solvent was evaporated to afford 0.499 g. of a white solid. Yield 34%. M.P.=195° C.

Analysis calculated for $C_{12}H_{15}N_3O$

Theory: C, 66.34; H, 6.96; N, 19.34; Found: C, 66.42; H, 5.47; N, 19.36.

EXAMPLE 2

3-Phenyl-4,5-dihydro-1,2,4-triazin-6(1H)-one

To 19.8 g. N-acetic acid-phenyl(methylthio)-imino ether dissolved in 200 ml ethanol was added dropwise 9.4 g. hydrazine hydrate dissolved in ethanol. The mixture was allowed to stir at about 25° C. for 2 hours, and then heated in a water bath at 70° C. for four hours and cooled. The precipitated solid was collected by filtration to yield 8.6 g. Yield 55%. M.P.=212°–217° C.

To 5.8 g. of methyl hippurate dissolved in 35 ml THF was added 3.9 g. of triphenylphosphine and 10.0 g. of carbon tetrachloride in 15 ml THF. The mixture was heated to about 50° C. for 6 hours and 3.0 g. of hydrazine hydrate was added. The mixture was refluxed for about 18 hours, cooled and poured into water. The solution was extracted with ethyl acetate, and the organic phase was then extracted with 1 N HCl. The acidic extract was neutralized with 6 N sodium hydroxide and the product was extracted with ethyl acetate. The organic phase was dried over anhydrous magnesium sulfate and concentrated under vacuum. The solid was recrystallized from methanol to yield about 0.200 g. of solid. Yield 4%. M.P.=212°–216° C.

Analysis calculated for $C_9H_9N_3O$

Theory: C, 61.70; H, 5.18; N, 23.99; Found: C, 61.54; H, 4.99; N, 23.74.

EXAMPLE 3

3-Phenyl-1,2,4-triazin-6(1H)-one

To 0.60 g. 3-phenyl-4,5-dihydro-1,2,4-triazin-6(1H)-one dissolved in 40 ml ethyl acetate was added 0.80 g. DDQ (2,3-dichloro-5,6-dicyano-1,4-benzoquinone). The solution immediately became green and was stirred at about 25° C. for 16 hours. The reaction mixture was then refluxed for 3 hours and cooled in an ice bath. The solid was collected and washed with three 50 ml portions of hexane. Yield 0.37 g. 64% Yield.

The following examples were prepared by the preferred synthetic route as described above.

EXAMPLE 4

3-(4-Chlorophenyl)-4,5-dihydro-1,2,4-triazin-6(1H)-one

71% Yield. M.P.=250°–260° C. d

Analysis calculated for $C_9H_8ClN_3O$

Theory: C, 51.57; H, 3.85; N, 16.91; Cl, 20.04; Found: C, 51.32; H, 4.03; N, 17.20; Cl, 19.94.

EXAMPLE 5

3-[3-(Trifluoromethyl)phenyl]-4,5-dihydro-1,2,4-triazin-6(1H)-one

55% Yield. M.P.=161°–163° C.

EXAMPLE 6

3-(1,1-Dimethylethyl)-4,5-dihydro-1,2,4-triazin-6(1H)-one

21% Yield. M.P. 227°–231° C.

Analysis calculated for $C_7H_{13}N_3O$

Theory: C, 54.17; H, 8.44; N, 27.08; Found: C, 54.27; H, 8.27; N, 26.93.

The novel compounds of the present invention have been found to display useful pre- and post-emergence herbicidal activity against a variety of weed species. The compounds may be applied directly to the plants when young, but are preferably applied to the soil prior to the emergence of the plant. The compounds may be either incorporated into the soil, by using a conventional disc or harrow prior to planting the seeds of the desired crop species, or by surface applying the compound to the soil before the plant emergence. In this latter procedure the compounds are merely permitted to leach into the soil with the assistance of rainfall, for example. While the compounds of the present invention display activity against a wide variety of weed species, they are most effective against lambsquarter, large crabgrass, pigweed, foxtail and morningglory.

The term "growth inhibiting amount", as defined herein, refers to an amount of a compound of the present invention which either kills or stunts the growth of the weed species for which control is desired. This amount will generally be from about 0.05 to about 15.0 pounds of 1,2,4-triazin-6-one per acre (about 0.056 to about 16.8 kg./ha.). The compounds are more preferably applied at rates of about 0.50 to about 8.0 pounds per acre (about 0.56 to about 8.96 kg./ha.). The exact concentration of compound required varies with the weed species to be controlled, type of formulation, soil type, climate conditions and the like.

The term "undesired plants", as defined herein, refers to both weeds and weed seeds which are present at the location to be treated with a compound of the present invention. The compounds can be applied to the soil to selectively control undesired plants by soil contact when the weed seeds are germinating and emerging. They can also be used directly to kill emerged weeds by direct contact with the exposed portion of the weed.

The compounds of the present invention may also be formulated with a suitable agriculturally-acceptable carrier. Such compositions will contain from about 0.1 to about 95.0 percent by weight of the active ingredient, depending on the composition desired. Sprayable formulations are preferred, mainly because of the rapidity and economy of application.

Dust compositions containing a compound of the present invention usually contain from about 0.1 to about 5 percent of the compound. Dusts are prepared by intimately mixing and finely grinding the compound with an inert solid such as ground montmorillonite clay, attapulgite clay, talc, ground volcanic rock, kaolin clay, or other inert, relatively dense, inexpensive substances.

The most convenient formulations are in the form of concentrated compositions to be applied by spraying as water dispersions or emulsions containing in the range from about 0.1 percent to about 10 percent of the compounds. Water-dispersible or emulsifiable compositions may be either solids usually known as wettable powders, or liquids usually known as emulsifiable concentrates.

A typical wettable powder comprises an intimate mixture of a compound of the invention, an inert carrier, and surfactants. The concentration of the active compound is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are chosen from among the sulfonated lignins, the condensed napthalenesulfonates, and the alkyl sulfates.

A typical emulsifiable concentrate comprises from about 0.1 to about 6 pounds of a compound of the invention per gallon of liquid, dissolved in a mixture of organic solvents and emulsifiers. The organic solven is chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, napthalenesulfonates, and nonionic surfactants such as alkylphenol adducts of polyoxyethylene, and are used at similar percentages as for wettable powders.

Solid, granular compositions are convenient for the application of compounds of this invention to the soil. Granules comprise a compound of the invention dispersed on a granular inert carrier such as coarsely ground clay of from about 0.1 to about 3 mm. particle size. The compound is most conveniently applied to the clay by dissolving it in an inexpensive solvent and applying the solution to the sized clay in an appropriate solids mixer.

The formulated compounds are applied to plants in the manners conventional in agricultural chemistry. Sprayable composiions are easily applied by any of the various types of sprayers available to the art. Self-propelled, tractor-mounted, and towed spray devices which apply the water-dispersed formulations through calibrated atomizing nozzles are available and effective. Metering applicators are also available which can apply accurately measured quantities of granular compositions to the soil. The operator of the application equipment need only take care to adjust the equipment to apply an amount of the water-dispersed or granular formulation per acre which supplies the desired application rate of the compound, and to apply the amount uniformly to the plants to be treated.

The herbicidal activity of representative compounds of the present invention is illustrated by the following experiments.

EXPERIMENT I

The compounds provided by this invention display herbicidal activity. The initial herbicide test was run at a test compound concentration of 15 lbs./acre (16.8 kg./ha.). In this test a standard sand:soil mixture (1:1) was sterilized at approximately 245° F. for 24 hours in an autoclave. Following sterilization the standard soil mixture was added to separate containers and tomato, large crabgrass and pigweed seeds were planted by row. Each container was fertilized with a 23-21-17 fertilizer.

The test compounds were formulated for application by dissolving 20 mg. of the compound into 2 ml of solvent. The solvent was prepared by placing 1.174 g of Toximul R and 0.783 g. of Toximul S (proprietary blends of anionic and nonionic surfactants manufactured by Stepan Chemical Company, Northfield, Illinois) into 100 ml of acetone and 100 ml of ethyl alcohol. The solvent/compound solution was diluted to 8 ml with deionized water. The solution was applied postemergence to some planted containers and preemergence to others using a modified deVilbiss atomizer. Postemergence treatment was made 11 to 13 days after planting while preemergence treatment was made one day after planting.

Following treatment the containers were moved to the greenhouse and watered as necessary. Observations were made 10 to 13 after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. Also, the various types of injury of each test species were coded as follows.

A = abscission of leaves
B = burned
C = chlorosis
D = death
E = epinasty
F = formation effects
G = dark green
I = increased plant growth
L = local necrosis
N = no germination
P = purple pigmentation
R = reduced germination
S = stunting
U = unclassified injury Table I presents the herbicidal activity of typical 1,2,4-triazin-6-ones of the present invention when evaluated in the herbicide test described above.

TABLE I

| | Herbicide Pretest at 15 lbs./acre (16.8 kg./ha.) | | | | | |
|---|---|---|---|---|---|---|
| | Preemergence | | | Postemergence | | |
| Example No. of Compound Tested | Tomato | Large Crab-grass | Pig-weed | Tomato | Large Crab-grass | Pig-weed |
| 1 | 1 | 1 | 1 | 1 | 1 | 1 |
| 2 | 3RS | 4RS | 3RS | 1 | 3BS | 3BS |
| 3 | 1 | 1 | 3RS | 2S | 1 | 1 |
| 4 | 1 | 4RS | 5N | 1 | 2S | 1 |

EXPERIMENT 2

The herbicidal activity of some of the compounds of the present invention was further evaluated at various application rates in a multiple species greenhouse test. Several additional weed and crop species were utilized to determine the herbicidal activity and selectivity of the test compounds. The compounds were formulated according to the procedure as described above, except that about 4 g./100 ml of the compound was dissolved in the surfactant containing solvent and about one part of the organic solution was diluted with 12 parts of water before application to the seed containers. Table II represents preemergence herbicidal test results administered at 8 lbs./acre (8.96 kg./ha.) or less, while Table III represents postemergence test data administered only at 8 lbs./acre.

TABLE II

| Example No. of Compound Tested | Rate of Appln. lbs/acre (kg/ha) | Preemergence | | | | | | | | |
|---|---|---|---|---|---|---|---|---|---|---|
| | | Crops | | | | | | | | |
| | | Corn | Cotton | Soybean | Wheat | Alfalfa | Sugar Beet | Rice | Cu-cumber | Tomato |
| 1 | 8.0(8.96) | 1 | | | | | | | | |
| 2 | 8.0(8.96) | 1 | | | | | | | | |
| | 8.0(8.96) | 4 | | | | | | | | |
| | 4.0(4.48) | 1 | 4 | 3 | 1 | 4 | 3 | 4 | 4 | 2 |
| | 2.0(2.24) | 1 | 1 | 1 | 1 | 1 | 1 | 1 | 1 | 1 |
| | 1.0(1.12) | 1 | 2 | 1 | 1 | 1 | 1 | 1 | 1 | 1 |
| 3 | 8.0(8.96) | 1 | | | | | | | | |
| 4 | 8.0(8.96) | 2 | | | | | | | | |
| 5 | 8.0(8.96) | 2 | | | | | | | | |
| | 4.0(4.48) | 3 | 1 | 2 | 1 | 1 | 3 | 3 | 3 | 1 |

TABLE II-continued

|   | 2.0(2.24) | 1 | 1 | 1 | 1 | 1 | 1 | 1 | 1 | 1 |
|---|---|---|---|---|---|---|---|---|---|---|
|   | 1.0(1.12) | 1 | 1 | 1 | 1 | 1 | 1 | 1 | 2 | 1 |
| 6 | 8.0(8.96) | 1 |   |   |   |   |   |   |   |   |

| Example No. of Compound Tested | Rate of Appln. lbs/acre (kg/ha) | Weeds | | | | | | | | | |
|---|---|---|---|---|---|---|---|---|---|---|---|
| | | Barnyard Grass | Lambsquarter | Large Crabgrass | Mustard | Pigweed | Foxtail | Wild Oat | Velvetleaf | Jimsonweed | Morningglory | Zinnia |
| 1 | 8.0(8.96) |   |   | 2 |   | 2 | 1 |   | 1 |   | 1 | 1 |
| 2 | 8.0(8.96) |   |   | 3 |   | 3 | 4 |   | 2 |   | 2 | 2 |
|   | 8.0(8.96) |   |   | 5 |   | 4 | 5 |   | 4 |   | 4 | 5 |
|   | 4.0(4.48) | 2 | 3 | 4 | 3 | 2 | 4 | 2 | 2 | 1 | 3 | 4 |
|   | 2.0(1.24) | 1 | 1 | 2 | 2 | 1 | 2 | 2 | 2 | 1 | 2 | 2 |
|   | 1.0(1.12) | 1 | 1 | 1 | 1 | 1 | 1 | 1 | 1 | 1 | 1 | 1 |
| 3 | 8.0(8.96) |   |   | 1 |   | 1 | 1 |   | 1 |   | 1 | 1 |
| 4 | 8.0(8.96) |   |   | 3 |   | 3 | 4 |   | 2 |   | 1 | 2 |
| 5 | 8.0(8.96) |   |   | 4 |   | 4 | 1 |   | 3 |   | 1 | 1 |
|   | 4.0(4.48) | 2 | 5 | 4 | 1 | 3 | 2 | 5 | 3 | 4 | 3 | 2 |
|   | 2.0(2.24) | 1 | 2 | 2 | 1 | 1 | 1 | 1 | 2 | 1 | 1 | 1 |
|   | 1.0(1.12) | 1 | 1 | 1 | 1 | 1 | 1 | 1 | 1 | 1 | 1 | 1 |
| 6 | 8.0(8.96) |   |   | 2 |   | 1 | 1 | 1 |   |   | 1 | 1 |

TABLE III

| | | Postemergence | | | | | | |
|---|---|---|---|---|---|---|---|---|
| Example No. of Compound Tested | Rate of Appln. lbs/acre (kg/ha) | Corn | Large Crabgrass | Pigweed | Foxtail | Velvetleaf | Morningglory | Zinnia |
| 1 | 8.0 (8.96) | 1 | 1 | 1 | 1 | 1 | 1 | 1 |
| 2 | 8.0 (8.96) | 1 | 1 | 1 | 1 | 1 | 1 | 1 |
| 3 | 8.0 (8.96) | 1 | 1 | 2 | 1 | 1 | 2 | 2 |
| 4 | 8.0 (8.96) | 1 | 1 | 2 | 1 | 2 | 2 | 2 |
| 5 | 8.0 (8.96) | 1 | 1 | 1 | 1 | 1 | 1 | 1 |
| 6 | 8.0 (8.96) | 1 | 1 | 2 | 1 | 1 | 2 | 1 |

I claim:

1. A compound of the formula

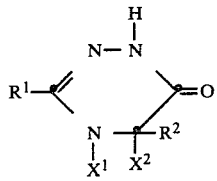

wherein:

$R^1$ represents $C_1$–$C_6$ alkyl, $C_3$–$C_6$ cycloalkyl, phenyl or phenyl monosubstituted with $C_1$–$C_3$ alkyl, $C_1$–$C_3$ alkoxy, halogen, $C_1$–$C_3$ haloalkyl or $C_1$–$C_3$ haloalkoxy;

$R^2$ represents hydrogen, $C_1$–$C_6$ alkyl or $C_3$–$C_6$ cycloalkyl; and $X^1$ and $X^2$ represent hydrogen atoms or combine to form a carbon-carbon bond;

with the provisos that when $R^2$ is methyl, $R^1$ is other than phenyl; and when $X^1$ and $X^2$ combine to form a carbon-carbon bond and $R^2$ is ethyl, $R^1$ is other than phenyl, 4-chlorophenyl and 4-methoxyphenyl.

2. A compound of claim 1 wherein $R^1$ is phenyl.

3. A compound of claim 2 wherein $R^2$ is hydrogen.

4. The compound of claim 3 which is 3-phenyl-4,5-dihydro-1,2,4-triazin-6(1H)-one.

5. A compound of claim 3 wherein $X^1$ and $X^2$ combine to form a carbon-carbon bond.

6. The compound of claim 5 which is 3-phenyl-1,2,4-triazin-6(1H)-one.

7. A compound of claim 2 wherein $R^2$ is $C_1$–$C_6$ alkyl.

8. The compound of claim 7 which is 3-phenyl-5-(1-methylethyl)-4,5-dihydro-1,2,4-triazin-6(1H)-one.

9. A compound of claim 1 wherein $R^1$ is phenyl monosubstituted.

10. A compound of claim 9 wherein $R^2$ is hydrogen.

11. The compound of claim 10 which is 3-(4-chlorophenyl)-4,5-dihydro-1,2,4-triazin-6(1H)-one.

12. The compound of claim 10 which is 3-[3-(trifluoromethyl)phenyl]-4,5-dihydro-1,2,4-triazin-6(1H)-one.

13. A compound of claim 1 wherein $R^1$ is $C_1$–$C_6$ alkyl.

14. A compound of claim 13 wherein $R^2$ is hydrogen.

15. The compound of claim 14 which is 3-(1,1-dimethylethyl)-4,5-dihydro-1,2,4-triazin-6(1H)-one.

16. A method for controlling undesired plants which comprises applying to the plants a growth inhibiting amount of a compound of claim 1.

17. A herbicidal composition which comprises a growth inhibiting amount of a compound of claim 1 and an agriculturally-acceptable carrier.

* * * * *